United States Patent
Brooke et al.

[11] Patent Number: 6,113,940
[45] Date of Patent: *Sep. 5, 2000

[54] CANNABINOID PATCH AND METHOD FOR CANNABIS TRANSDERMAL DELIVERY

[76] Inventors: Lawrence L. Brooke, 3696 Frei Rd., Sebastopol, Calif. 95472; Cal C. Herrmann, 5621 Sierra Ave., Richmond, Calif. 94805

[ * ] Notice: This patent issued on a continued prosecution application filed under 37 CFR 1.53(d), and is subject to the twenty year patent term provisions of 35 U.S.C. 154(a)(2).

[21] Appl. No.: 09/056,848

[22] Filed: Mar. 3, 1998

Related U.S. Application Data
[60] Provisional application No. 60/039,603, Mar. 3, 1997.
[51] Int. Cl.⁷ .............................. A61F 13/02; A61L 15/16
[52] U.S. Cl. ............................................ 424/449; 424/448
[58] Field of Search ...................................... 424/448, 449

[56] References Cited

U.S. PATENT DOCUMENTS

| | | | |
|---|---|---|---|
| 4,839,174 | 6/1989 | Baker et al. | 424/447 |
| 4,943,435 | 7/1990 | Baker et al. | 524/448 |
| 5,135,753 | 8/1992 | Baker et al. | 424/435 |
| 5,540,934 | 7/1996 | Touitou | 424/450 |

OTHER PUBLICATIONS

Metabolic Rate of Tetrahydrocannabinol, S. Agurell, et al., pp. 18–19 (1972).

GLC and HPLC Analyses of Cannabinoids in Biological Fluids and Applications, Gerrett, et al., pp. 13–16 (1979).

Developments in Cannabinoid Analyses of Body Fluids: Implications for Forensic Applications, R. Hawks, pp. 123–133 (1984).

The Pharmacology of Cannabis in Animals, W. Paton, et al., pp. 191–195 (1973).

Clinical Aspects of Cannabis Chemistry, W. Paton, et al., pp. 357–362 (1973).

The Pharmacokinetics of Delta–9–Tetrahydrocannabinol in Man After Simultaneous Intravenous and Oral Administration, B. Sadler, et al., pp. 227–236 (1984).

Separation of Acid and Neutral Cannabinoids in *Cannabis Sativa* L. Using HPLC, J. Turner, et al., pp. 79–88 (1984).

Chemistry, Toxicology and Psychic Effects of Cannabis, C. Waller, pp. 473–500 (1984).

Analytical Aspects of Cannabis Chemistry, M. Willinsky, pp. 138–140 (1973).

*Primary Examiner*—Thurman K. Page
*Assistant Examiner*—S. Howard
*Attorney, Agent, or Firm*—Kenneth J. Hovet

[57] ABSTRACT

A transdermal structure is provided for delivering cannabis chemical(s) to one's bloodstream. The structure comprises a backing layer which carries the cannabis chemical(s). The chemicals are contained in a film on the backing layer or within a cavity formed in the backing layer. Alternatively, an opening in a secondary layer that overlies the backing layer may be used to create the cavity. The structure is applied to one's skin so that the cannabis chemicals are in contact with the skin. A polymer material which is mixed with the cannabis and placed in the cavity or a membrane over the cavity may be used to control the flow of cannabis chemical(s) into the bloodstream. In an alternative embodiment, a porous material impregnated with cannabis chemical(s) may be used to hold the chemical(s) in the cavity.

20 Claims, 1 Drawing Sheet

CANNABINOID PATCH AND METHOD FOR CANNABIS TRANSDERMAL DELIVERY this application claims priority from Provisional Application Ser. No. 60/039,603 which was filed Mar. 3, 1997.

FIELD OF THE INVENTION

This invention pertains to methods and products for the transdermal administration of cannabis. More particularly, this invention concerns a system for delivering effective dosages of cannabis to one's bloodstream.

BACKGROUND OF THE INVENTION

Methods and products for transdermally administering particular chemicals are known in the art. Several U.S. patents have issued for the transdermal application of chemicals, most recently for nicotine. This invention expands the concept of transdermal delivery to cannabis, since the unique social and chemical characteristics of cannabis lend it to such an application.

Several medicinal uses have been found for the active ingredients of cannabis, including the ingredients tetrahydrocannabinol (THC), cannabinol (CBN), cannabidiol (CBD) and cannabichromene (CBC). The medicinal uses of cannabis include (1) treatment of nausea and pain associated with cancer and chemotherapy; (2) nausea, pain and wasting associated with AIDS; (3) arthritis and rheumatism; (4) glaucoma; (5) migraines; (6)muscle spasticity associated with multiple sclerosis and paralysis; (7) alcohol and narcotics withdrawal; (8) stress and depression; (9) asthma; and (10) epileptic seizures. Despite the many proven or suspected benefits of cannabis, legal and social barriers prevent its widespread use. Currently, only Marinol, a synthetic form of THC is available by prescription to patients. One purpose of the present invention is to extend the widespread medicinal use of cannabis without triggering the legal or social barriers associated with prescription of the drug.

The chemical composition of cannabis and its active ingredients allow for its transdermal delivery. For instance, the primary active ingredient of cannabis is THC, which is effective in vito at very low doses. Due to its high liphophilicity, THC exhibits strong tendency to bind to tissue and protein, making transdermal application possible. Fatal misuse has also been a concern in previous transdermal applications, but cannabinoids are rarely fatal when overdosed. Furthermore, THC is rapidly metabolized in the body, such that concentration levels of the chemical in the bloodstream decreases rapidly if administered through traditional methods. In contrast, a transdermal application allows for small dosages of THC to be administered over an extended period of time, thereby allowing the concentration levels of the chemical to remain relatively steady in the bloodstream.

SUMMARY OF THE INVENTION

The present invention comprises a structure, such as a skin patch, bandage, covering or related assembly of materials, which can contain and administer an effective amount of cannabis or its chemical constituents during a predetermined period of time. One purpose of the structure is to allow for controlled delivery of the active chemicals, such that plasma levels of the chemicals may be controlled in a safe, convenient and effective manner for the patient.

This invention also comprises the method of treating a patient with a transdermal cannabis preparation. Most conveniently, this is accomplished by application of the transdermal structure described herein. Antecedent or conjunctive steps for increasing the permeability of the patient's skin may further comprise the method for transdermally applying cannabis.

The invention includes a reservoir means for retaining and dispersing the active ingredients of the cannabis. In one embodiment of the invention, the reservoir means includes a rate controlling means overlying a cavity formed in a backing layer containing the cannabis. The rate controlling means regulates flux, hereinafter defined as the volumetric flow rate of the cannabis chemicals to the skin.

The rate controlling means may comprise a nonporous polymer membrane for regulating the flux. Alternatively, the rate controlling means may comprise a porous material made of elements suitable for controlling the diffusion rate of cannabis. Examples of suitable porous materials include rubber or plastic layers soaked in an aqueous ionic solution.

The reservoir means may also comprise a polymer matrix material which suspends the cannabis and releases it in a controlled manner. The flux of the polymer matrix material may further be regulated by a rate controlling membrane.

DESCRIPTION OF THE PREFERRED EMBODIMENTS

"Cannabis" as used herein means pure cannabis or any compound or chemical component thereof, including tetrahydrocannabinol (THC), cannabinol (CBN), cannabidiol (CBD) and cannabichromene (CBC). The word "structure" means one or more layers of material suitable for attachment to one's skin, including strips or patches of fabric, plastic, metal foil, rubber, resin film, natural membranes and laminates of any one or combination of the above.

Figure 1:
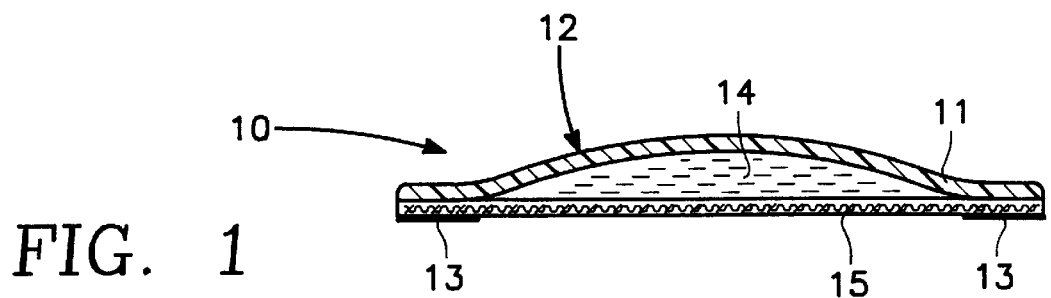
FIG. 1 shows an embodiment of the invention comprising a backing layer, a reservoir of cannabis and a rate controlling membrane.

With reference to FIG. 1, a cannabinoid structure 10 is depicted comprising a backing layer 11, a reservoir means 12 and an adhesive means 13. Since the cannabinoid structure may contain several active ingredients at variable concentrations, including THC and CBD, the listed parameters and specific materials may be varied to accommodate administration of specific ingredients or dosages.

The backing layer 11 functions to protect the contents of the structure from environmental conditions, such as evaporation or abrasion. The backing layer 11 may have multiple linings, with the interior lining adjoining the reservoir means.

To protect the structure while in use, the inner surface of the backing layer should not interact with the cannabis ingredients. For instance, THC should not adjoin silicone-based materials or Teflon, since THC is known to bind with such surfaces. Examples of materials having potential for comprising an effective backing layer include aluminized polyester and polybutene nonwoven polyester.

With further reference to FIG. 1, the reservoir means comprises a cavity 12 in the backing layer containing a cannabis preparation 14. A rate controlling membrane 15 overlies the cavity for regulating dispersion of the cannabis chemicals. The cavity comprises a round or oval-shaped convex area in the backing layer. It is sized to accommodate the selected volume of cannabis preparation 14. As shown in FIG. 1, the preparation comprises a liquid or gel carrier combined with the cannabis chemical(s).

Effective gel or liquid carriers for the cannabis may include carbon tetrachloride, or ethanolic solutions of resin and pyrahexyl mixed with THC. Other potential carriers include Tween 80 or petrol ether. In all cases, the carrier material should be inert to the cannabis chemicals and permit easy migration of the preparation to the patient's skin.

The rate controlling means is located directly adjacent to the patient's skin. Its function is to control the flux of cannabis from the reservoir to the skin. A preferred rate controlling means may comprise a polymer membrane having a predetermined permeability and thickness for allowing the release of effective amounts of cannabis continuously for several hours.

Once an appropriate polymer is chosen, the membrane may be formed by preparing a homogenous solution containing the polymer and an organic solvent. The solution is cast upon a glass plate or equivalent, where the solvent is evaporated from the solution. The evaporation of the solvent results in a film which comprises the membrane, and the thickness of the membrane can be varied as required by the desired cannabis chemical flux.

Alternatively, the rate controlling membrane may be purchased in film form. The cannabinoid patch may then be prepared by heat sealing the backing layer 11 around the perimeter of the membrane with the cavity in between.

Factors to consider in determining an appropriate polymer membrane include the polymer's resistance to deterioration from cannabis, and the polymer's permeability towards cannabis. Previous transdermal applications have used dense nonporous materials as the polymer membrane, including commercial polyethylenes such as Sclairfilm. Nonporous polymer materials offer the advantage of administering the drug over the greatest period of time. However, nonporous polymer materials are not necessarily optimally suited for a transdermal cannabinoid structure, since cannabis components have relatively large molecular sizes and exhibit unique chemical interactions such as binding with some materials.

The rate controlling means may also comprise porous materials which are fastened to the backing layer 11 with adhesives. The cavity is then suspended in between the backing layer and the porous material. Prior experimentation has shown that cannabis ingredients such as THC diffuse rapidly in certain porous materials such as rubber and plastic. Furthermore, THC is insoluble with many solutions, including aqueous and ionically charged solutions.

An application of an ionic aqueous solution to a porous material will hinder the diffusion rate of THC through the material and decrease the resulting bioavailability of the chemical flux. Therefore, an appropriate combination of porous THC absorbing material, combined with a solution that is insoluble with THC, can form a suitable rate control means for the chemical diffusion flux. An example of such a rate controlling membrane includes mixing salt water with a rubber surface that covers the cavity. The thickness of the rubber, the concentration of the salt water, and the amount of available chemicals in the cavity are determined experimentally to create a desired diffusion flux of THC to the patient's skin. Evaporation of necessary fluids may be prevented by a protective backing layer.

With further reference to FIG. 1, an adhesive means 13 may be integrated with the cannabis assembly to hold the structure in contact with the user's skin. The adhesive means should be compatible with cannabis, and should not hinder movement of the cannabis into the patient's skin. The adhesive means may comprise one or more film strips of pressure-sensitive material, such as an acrylate based adhesive, having amine resistance. The adhesive strips can be cast directly onto the skin-facing side of the backing layer or the rate controlling membrane. Alternatively, medical adhesive tape may simply be applied over the backing layer's outer surface, thereby securing the structure to the skin of the patient.

Figure 2:
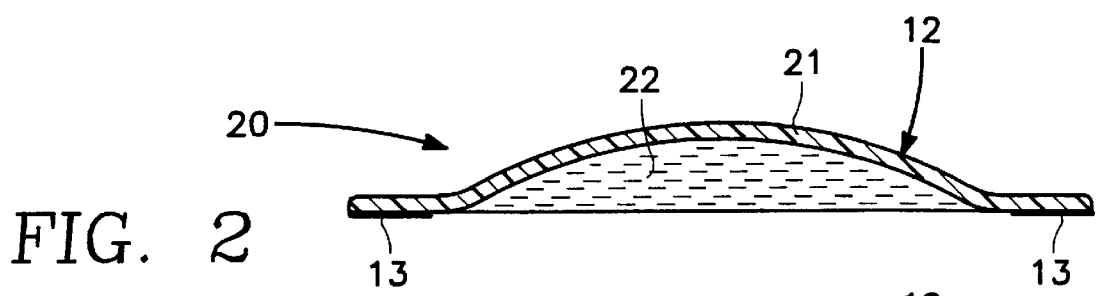
FIG. 2 shows an embodiment of the invention comprising a backing layer with a reservoir of viscous cannabis/polymer material.

With reference to FIG. 2, an alternative polymer structure 20 is shown. This structure is similar to FIG. 1 in that it utilizes a backing layer 21 having a cavity 12. Within the cavity is a matrix composition 22 comprising cannabis suspended in a polymer solution. In this embodiment, the matrix material serves as both the cannabis carrier and the diffusion mechanism for administration of the cannabis chemical(s). As such, use of a rate controlling membrane is not essential.

The matrix composition 22 may be prepared by forming a solution comprising a solvent mixed with a polymer matrix material. Cannabis, preferably in liquid form, is homogeneously mixed with the polymer matrix solution. The concentration of cannabis may be varied depending on the desired chemical load for the specific cannabinoid application. The resulting solution is cast on the backing layer 21 where the solvent is evaporated to create a polymer film. In this variation, the cavity 12 may not be necessary.

The above-mentioned polymer matrix may also be formed apart from the backing layer 21 by attaching a single-sided occlusive medical tape to one face of the matrix material 22. The matrix thickness determines the upper limit of the cannabis concentration, since overloading the cannabis concentration will prevent the film from forming. Examples of suitable polymers and carrier materials for forming the matrix material include acrylic adhesives, polyurethanes, polymethyl methacrylate, polybutyl methacrylate and ethylene-acrylic acid polymers. Suitable solvents include tetrahydrofuran, dimethysulfoxide and dimethylformamide.

Figure 3:
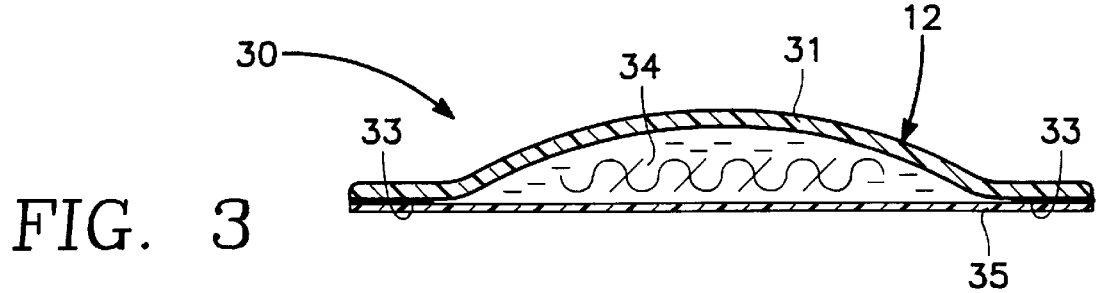
FIG. 3 is another embodiment of the invention comprising a backing layer and a reservoir containing a matrix material impregnated with cannabis and covered with a protective removable overlay.

With reference to FIG. 3, a matrix structure 30 is shown. This embodiment comprises a backing 31 having an offset portion forming a pocket or reservoir 12 to contain a porous material 34 impregnated with predetermined amounts of the cannabis preparation. Around the reservoir periphery is a layer of adhesive 33. To seal-in the preparation, a removable protective overlay sheet 35 is adhered to the adhesive.

The porous matrix material 34 may comprise an open pore structure such as a foamed polyurethane or sponge. In such case, the cannabis preparation will be contained within the pore structures. Alternatively, the material may include a pad of an open weave fabric such as gauze. In such case, the cannabis preparation would be held within the interstices between the fabric fibers.

The appropriate cannabis concentration must be determined on an individual basis. While cannabinoids are rarely lethal, an overdose can produce undesirable and damaging side effects. One variable that may effect the dosage of the viscous liquid or gel preparations 14 or matrix material 22, is the patient's skin permeability, which may vary twenty fold or more among individuals.

For a more effective or predictable method of transdermal delivery, the cannabinoid structure may be used in conjunction with an auxiliary means for facilitating a transdermal application. An example of an auxiliary means is the application of a patch containing a low dosage on a portion of the patient's skin containing artificially induced pores, such as those created by pin pricks.

Another auxiliary means may comprise a chemical carrier that increases the permeability of the user's skin with respect to cannabis. The chemical carrier may be incorporated into the cannabis flux, or be administered to the patient's skin as a precedent step to the cannabis application. Examples of suitable carriers include ionically charged materials which polarize the skin's molecules and increase the skin's permeability through ionic force. Another example is a solution of DMSO (dimethyl sulfoxide). This material may be incorporated into the cannabis preparation in volumetric concentrations of up to about ten percent.

Figure 4:
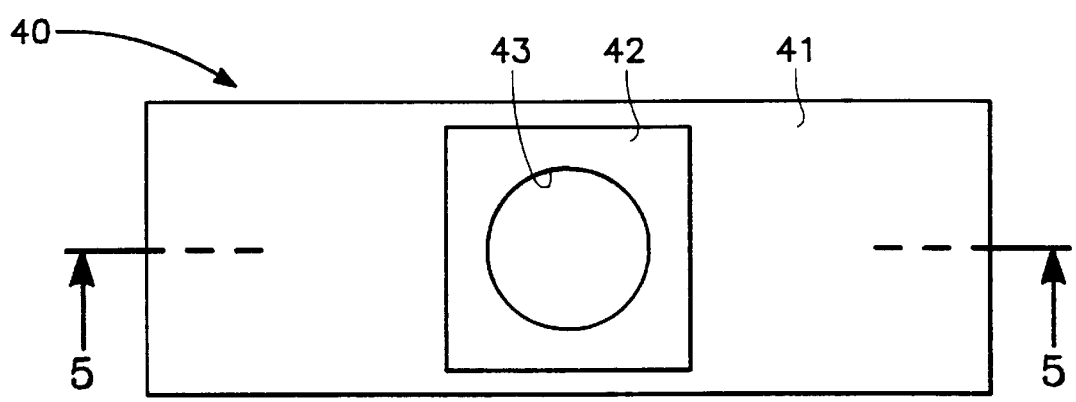
FIG. 4 is top plan view of another embodiment of the invention comprising a backing layer with a secondary overlay having an opening containing cannabis covered with a protective removable overlay.
Figure 5:
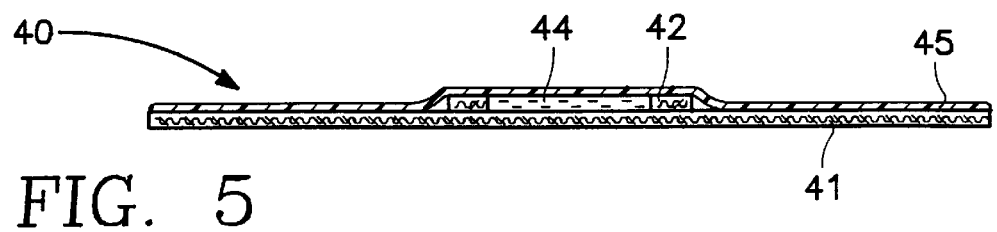
FIG. 5 is a cross-sectional view taken along lines 5—5 of FIG. 4.

FIGS. 4 and 5 illustrate an alternative laminate structure 40 which utilizes a secondary overlay to create a cannabis holding means. As shown, secondary layer 42 is fused, bonded or adhered, by means known in the art, to a larger backing strip 41. The secondary layer has an opening 43 which forms a retention cavity with the backing strip for the cannabis preparation 44. The thickness of the secondary layer and diameter of the opening will determine the maximum volume amount of preparation that can be contained within the opening.

Upper surfaces of the backing strip and secondary layer may include an adhesive film for adhering the strip to a patient's skin. A removable sheet 45, shown in FIG. 5, is used to sealingly enclose the cavity and protect the overall strip prior to use.

An example of forming the cannabis preparation involves drying and grinding to a fine powder a cannabis plant material. This powder is then refluxed with alcohol or petroleum for three to four hours to separate the cannabis oils from the plant cellulose mass. The resultant extract is further purified and concentrated by removing tars and waxes with an alcohol petroleum ether and water wash. The remaining purified oil is separated from residual solvent through distillation.

The purified cannabis oil is similar to honey in color and consistency. It is mixed with a vehicle such as DMSO or other known transdermal agent in the desired concentration to produce the cannabis preparation. This mixture may be optionally heated and placed within the previously described reservoir means. Thereafter, a protective sheet may be applied and the finished assembly is sterile packaged for storage, distribution and sale.

In a test with two subjects, a structure similar to FIG. 2 was prepared using about 0.2 gram of cannabis oil and about 0.02 grams of DMSO. The structure was applied to the underside of the wrist of two human subjects. In about ten minutes, the soothing affect of the medication was observed. No side effects were detected and the affects of the cannabis were felt for four to six hours.

While the invention has been described with respect to preferred embodiments, it will be clear to those skilled in the art that modifications and improvements may be made to the invention without departing from the spirit and scope of the invention. Therefore, the invention is not to be limited by the specific illustrative embodiments, but only by the scope of the appended claims.

We claim:

1. A method of delivering cannabis to the bloodstream of a person comprising the steps of:

A. Providing a transdermal preparation containing cannabis;

B. Providing a backing layer selected from the group consisting of a patch, strip, bandage and covering for holding said transdermal preparation;

C. Placing an effective amount of said transdermal preparation onto said backing layer; and, D. Attaching said backing layer to the skin of said person so that said transdermal preparation is in contact with said skin.

2. The method of claim 1 wherein step A comprises combining said cannabis with a transdermal carrier.

3. A transdermal structure containing cannabis comprising a backing layer selected from the group consisting of a patch, strip, bandage or covering having a reservoir means for holding a transdermal cannabis preparation; and, a transdermal preparation contained in said reservoir means.

4. The structure of claim 3 wherein the reservoir means is any one or combination of a member of the group consisting of a cavity, matrix material and film.

5. The structure of claim 4 wherein said matrix material is selected from the group consisting of an open pore material, open weave fabric and a membrane.

6. The transdermal structure of claim 4 wherein said reservoir means comprises a convex portion of said backing layer.

7. The structure of claim 4 wherein a secondary layer is attached to said backing layer, said secondary layer having an opening which forms a retention cavity with said backing layer for holding said transdermal preparation.

8. A structure for administering cannabis to one's skin, comprising:

at least one layer of backing material suitable for attachment to one's skin; and, a cannabis preparation on said backing material, said preparation being capable of delivering an effective amount of cannabis into said skin.

9. The structure of claim 8 wherein said backing material is any one or combination of a member selected from the group consisting of fabric, plastic, metal foil, rubber, resin film and membranes.

10. The structure of claim 8 wherein said backing material includes a reservoir means for retaining said cannabis preparation.

11. The structure of claim 10 wherein said reservoir means comprises a polymer matrix attached to said material, said cannabis preparation being suspended in said polymer matrix.

12. The structure of claim 10 wherein said reservoir means comprises a cavity formed in said backing material, said cannabis preparation being contained in said cavity.

13. The structure of claim 12 wherein a rate controlling means overlies said cavity for regulating the flow of cannabis preparation to said skin.

14. The structure of claim 13 wherein said rate controlling means comprises a member selected from the group consisting of a porous membrane, nonporous membrane, polymer film, polymer membrane.

15. The structure of claim 8 wherein said cannabis preparation comprises a liquid or gel carrier combined with cannabis chemicals.

16. The structure of claim 11 wherein said polymer matrix comprises a film which has been cast upon said backing layer.

17. The structure of claim 10 wherein said reservoir means comprises a member selected from the group consisting of an open pore structure and an open weave fabric.

18. The structure of claim 8 wherein said backing material includes adhesive means for attaching said structure to one's skin.

19. The method of claim 1 wherein said structure includes an adhesive and step D is carried out by adhering said structure to said skin.

20. The method of claim 1 wherein after step D, maintaining said transdermal preparation in contact with said skin for an effective period of time.

* * * * *